(12) United States Patent
Goodwin, Jr. et al.

(10) Patent No.: US 10,660,687 B2
(45) Date of Patent: May 26, 2020

(54) DRIVER TOOL AND METHOD

(71) Applicant: A&E Advanced Closure Systems, LLC, Los Angeles, CA (US)

(72) Inventors: Robert A. Goodwin, Jr., Marquette, MI (US); Matthew P. Gephart, Marquette, MI (US)

(73) Assignee: A&E Advanced Closure Systems, LLC, Los Angeles, CA (US)

(*) Notice: Subject to any disclaimer, the term of this patent is extended or adjusted under 35 U.S.C. 154(b) by 41 days.

(21) Appl. No.: 16/016,115

(22) Filed: Jun. 22, 2018

(65) Prior Publication Data

US 2019/0000523 A1 Jan. 3, 2019

Related U.S. Application Data

(60) Provisional application No. 62/527,692, filed on Jun. 30, 2017.

(51) Int. Cl.
*A61B 17/88* (2006.01)
*A61B 90/00* (2016.01)
*A61B 17/86* (2006.01)
*A61B 17/00* (2006.01)

(52) U.S. Cl.
CPC ...... *A61B 17/8888* (2013.01); *A61B 17/8875* (2013.01); *A61B 90/03* (2016.02); *A61B 17/86* (2013.01); *A61B 17/8615* (2013.01); *A61B 2017/00862* (2013.01); *A61B 2090/031* (2016.02)

(58) Field of Classification Search
CPC .......... A61B 17/8875; A61B 2090/031; B25B 23/142; B25B 23/1427
See application file for complete search history.

(56) References Cited

U.S. PATENT DOCUMENTS

| 2,378,956 | A | | 6/1945 | Thorner |
| 2,439,980 | A | * | 4/1948 | Livermont .......... B25B 23/1427 464/23 |
| 2,561,136 | A | | 7/1951 | Richardson |
| 2,797,564 | A | * | 7/1957 | Bonneau ............. B25B 23/1427 464/38 |
| 3,535,958 | A | | 10/1970 | Larson |

(Continued)

FOREIGN PATENT DOCUMENTS

| JP | 59163466 U | 11/1984 |
| JP | 61071375 U | 5/1986 |

(Continued)

OTHER PUBLICATIONS

PCT Search Report and Written Opinion from International Patent Application No. PCT/US18/39270 dated Sep. 18, 2018; 11 pages.

(Continued)

*Primary Examiner* — Nicholas W Woodall
(74) *Attorney, Agent, or Firm* — Fitch, Even, Tabin & Flannery LLP

(57) ABSTRACT

In one aspect, a surgical driver is provided that includes a driver shaft, a handle rotatably connected to the driver shaft, and a resilient, elongate pin extending transverse to the driver shaft. The pin is operably engaged with the driver shaft and the handle so that torque applied to the handle causes turning of the driver shaft. The pin is configured to deflect to limit the torque applied to the driver shaft.

32 Claims, 15 Drawing Sheets

(56) References Cited

U.S. PATENT DOCUMENTS

| | | | |
|---|---|---|---|
| 3,640,141 A | 2/1972 | Hollingsead | |
| 4,092,753 A | 6/1978 | Fuhrmann | |
| 4,572,041 A | 2/1986 | Rissmann | |
| 5,354,299 A | 10/1994 | Coleman | |
| 5,571,014 A * | 11/1996 | Gregory, Jr. | A61C 8/0089 433/126 |
| 5,626,474 A | 5/1997 | Kukla | |
| 6,439,086 B1 | 8/2002 | Bahr | |
| 7,383,756 B1 | 6/2008 | Liu | |
| 7,938,046 B2 | 5/2011 | Nino | |
| 7,992,472 B2 | 8/2011 | Gao | |
| 8,028,608 B2 | 10/2011 | Sixto, Jr. | |
| 8,051,751 B2 * | 11/2011 | Huang | B25B 23/1427 81/467 |
| D652,137 S | 1/2012 | Nino | |
| 8,276,487 B2 | 10/2012 | Wengreen | |
| 8,317,791 B2 | 11/2012 | Phan | |
| 8,757,035 B2 | 6/2014 | Kerboul | |
| 9,504,528 B2 | 11/2016 | Ivinson | |
| D779,058 S | 2/2017 | Nino | |
| D779,060 S | 2/2017 | Nino | |
| D779,663 S | 2/2017 | Nino | |
| 2001/0004610 A1 | 6/2001 | Casutt | |
| 2009/0255386 A1 | 10/2009 | Liao | |
| 2010/0275744 A1 | 11/2010 | Wengreen | |
| 2011/0000347 A1 | 1/2011 | Stark | |
| 2011/0056341 A1 | 3/2011 | Lai | |
| 2011/0094354 A1 | 4/2011 | Lai | |
| 2012/0227221 A1 | 9/2012 | Whitaker | |
| 2014/0276893 A1 | 9/2014 | Schaller | |
| 2014/0277203 A1 | 9/2014 | Atoulikian | |
| 2014/0366691 A1 | 12/2014 | Ivinson | |
| 2015/0202018 A1 | 7/2015 | Schaller | |
| 2015/0342693 A1 | 12/2015 | Ivinson | |
| 2016/0184043 A1 | 6/2016 | Ivinson | |
| 2017/0035485 A1 | 2/2017 | Ivinson | |
| 2017/0065322 A1 | 3/2017 | Prado | |
| 2017/0105813 A1* | 4/2017 | Rash | A61B 17/8875 |

FOREIGN PATENT DOCUMENTS

| | | |
|---|---|---|
| JP | 2001121444 A | 5/2001 |
| KR | 1019980008465 A | 4/1998 |
| WO | 9942252 A1 | 8/1999 |
| WO | 2011139902 A2 | 11/2011 |
| WO | 2013081934 A1 | 6/2013 |
| WO | 2014012035 A9 | 1/2014 |

OTHER PUBLICATIONS

Proto Labs, Inc.; Protomold® December Design Tip: The Skinny on Living Hinges; from http://www.protomold.com/Design_Tips/UnitedStates/2010/2010-12_designtips/default.htm; Dec. 2010; 3 pages.

* cited by examiner

DRIVER TOOL AND METHOD

CROSS-REFERENCE TO RELATED APPLICATION

This application claims the benefit of U.S. Provisional Patent Application No. 62/527,692, filed Jun. 30, 2017, which is hereby incorporated by reference in its entirety.

FIELD

The disclosure relates to surgical instruments and, more specifically, to surgical instruments for driving bone screws or other elements of medical devices.

BACKGROUND

Surgical drivers are known for driving bone screws into bone. Surgical drivers may also be used to adjust elements of medical devices, such as adjusting a set screw of a bone plate. Some surgical drivers have torque limiting features that limit the risk of overtightening, for example, a screw being driven into bone. These prior surgical drivers may have complicated mechanisms to limit torque that increase the cost of the surgical driver. Due to their cost, the surgical driver may be reused in different procedures. The surgical driver is cleaned before being reused, which involves additional resources to clean the surgical driver and keep track of the surgical driver within, for example, a hospital.

SUMMARY

In accordance with one aspect of the present disclosure, a surgical driver is provided including a driver shaft, a handle rotatably connected to the driver shaft, and a resilient elongate pin. The resilient elongate pin extends transverse to the driver shaft and is operably engaged with the driver shaft and handle such that torque applied to the handle for turning the handle causes turning of the driver shaft. The pin is configured to deflect to limit the torque applied to the driver shaft. The elongate pin deforms in a manner similar to a beam such that the deformation of the pin in response to torque applied to the handle is predictable and highly accurate.

In another aspect, a surgical driver is provided that includes a driver shaft, a handle rotatably connected to the driver shaft, and a resilient member operably engaged with the driver shaft and handle. The surgical driver includes a plurality of raised ridge members each having a ramp surface for deflecting the resilient member upwardly and an upper surface along which the deflected resilient member travels as the handle turns relative to the driver shaft. Each raised ridge member includes a vertical surface extending at a different inclination relative to the upper surface than the ramp surface and a corner connecting the top surface and the vertical surface. A lower surface extends between adjacent ones of the raised ridge members, with the resilient member striking the lower surface as the resilient member rebounds from the deflected configuration. The impact of the resilient member snapping downward from the upper surface of one of the raised ridge members and against the adjacent lower surface provides a tactile and audible indication of the resilient member having deformed in response to the torque applied to the handle exceeding a predetermined torque limit of the surgical driver.

In accordance with another aspect of the present disclosure, a surgical driver is provided that includes a driver shaft, a handle rotatably coupled to the driver shaft, and a resilient member. The resilient member is operably engaged with the driver shaft and the handle such that torque applied to the handle for turning the handle causes turning of the driver shaft. The surgical driver further includes a plurality of pockets each configured to receive the resilient member therein with the resilient member spaced from surfaces of the pockets prior to application of torque to the handle. In this manner, the pockets generally do not apply a load against the resilient member prior to a user applying torque to the handle. This limits creep in the resilient member during storage and transit of the surgical driver and preserves the accuracy of the device. The pockets include ramp surfaces adapted to deflect the resilient member out of the pockets to limit torque applied to the handle when the handle is turned. In one form, the ramp surface of a pocket deflects the resilient member out of the pocket in response to the torque applied to the handle exceeding a predetermined torque limit for the surgical driver.

DETAILED DESCRIPTION

Figure 1:
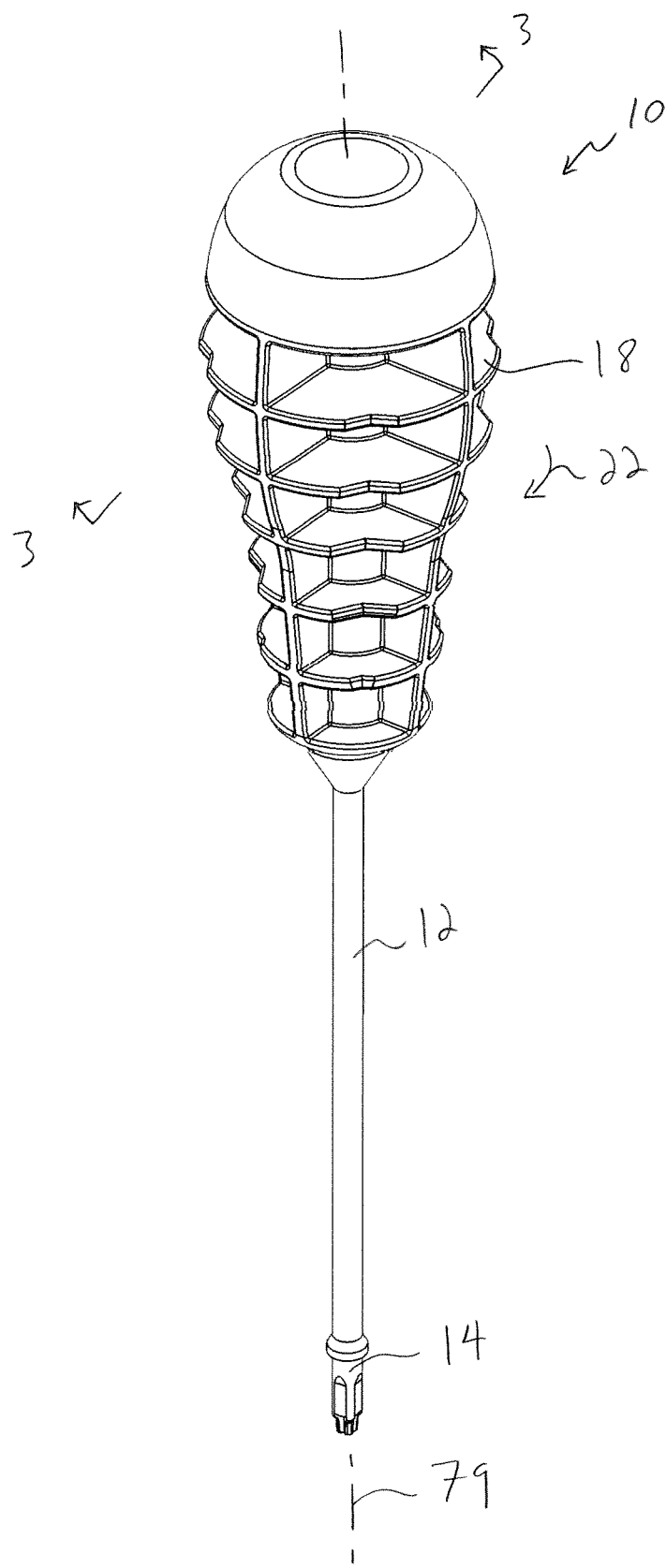
FIG. 1 is a perspective view of a torque limiting surgical driver having a handle that is rotatable relative to a shaft of the driver.
Figure 2:
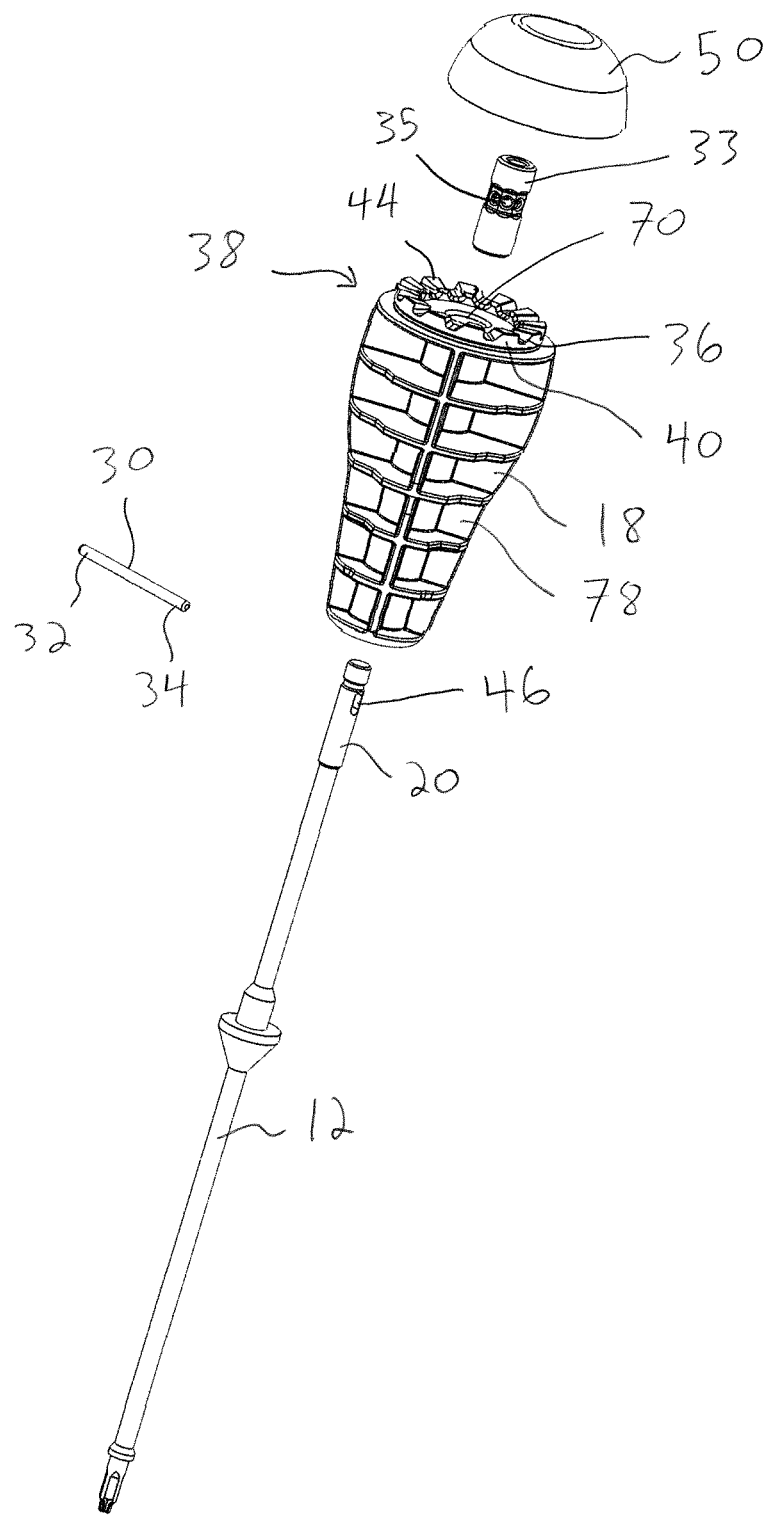
FIG. 2 is an exploded view of the driver of FIG. 1 showing a body and a cap of the handle that are retained on the shaft.
Figure 3:
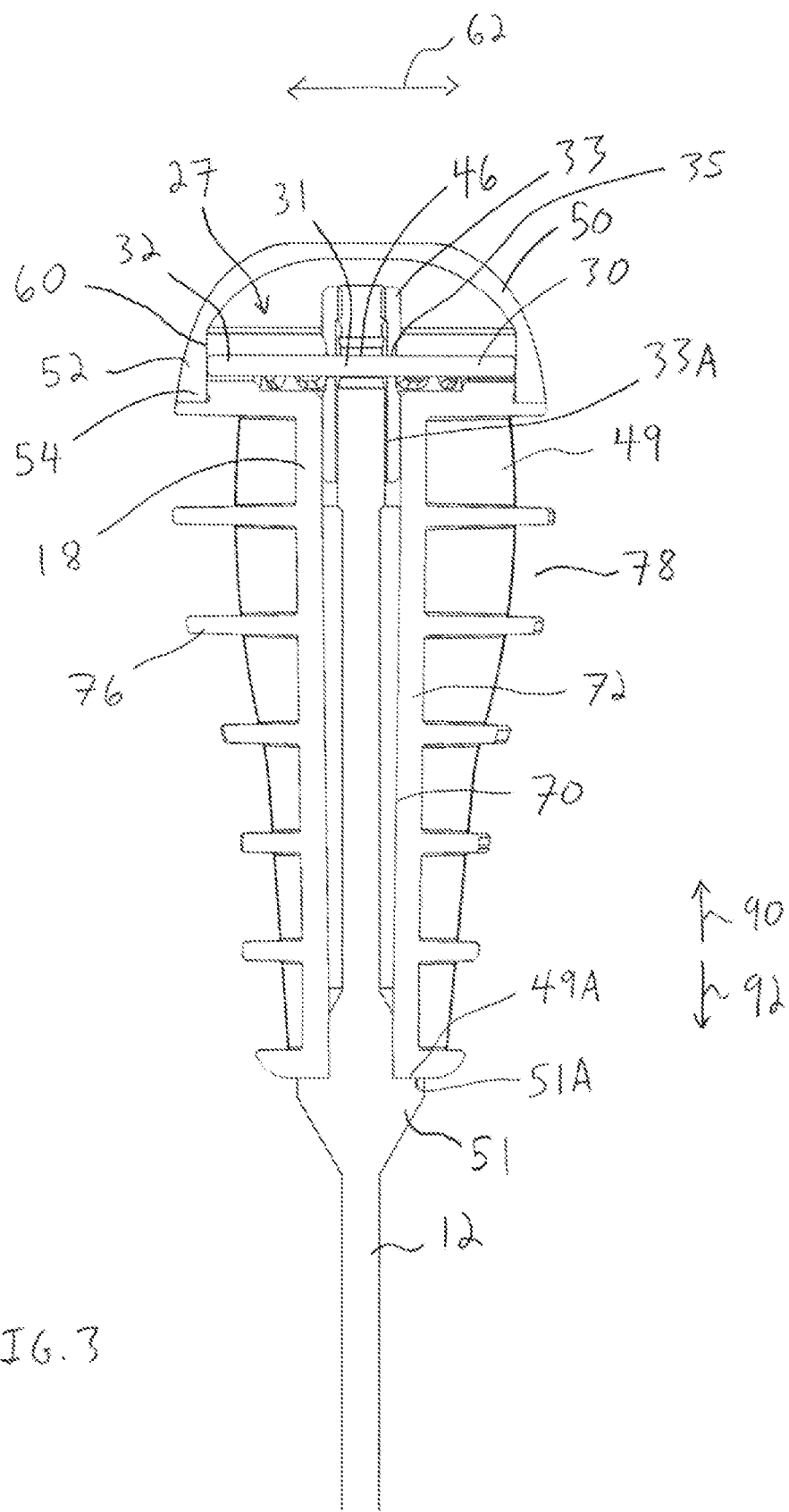
FIG. 3 is a cross-sectional view taken across line 3-3 in FIG. 1 showing the handle body held in position along the shaft by a pin extending through a nut and an upper end portion of the shaft.
Figure 8:
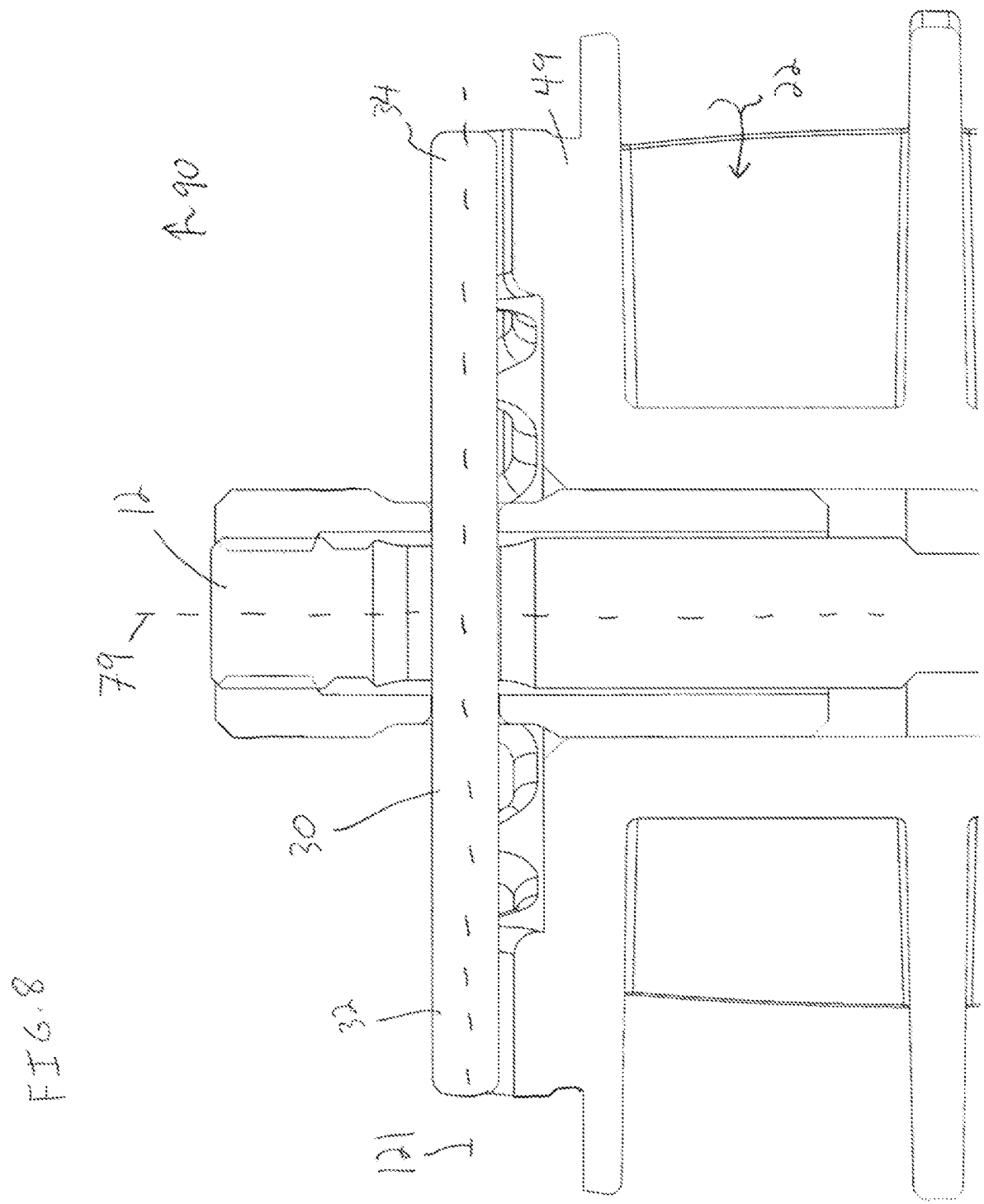
FIG. 8 is a cross-sectional view taken across line 8-8 in FIG. 6 showing the pin in the undeflected configuration before torque is applied to the handle.
Figure 9:
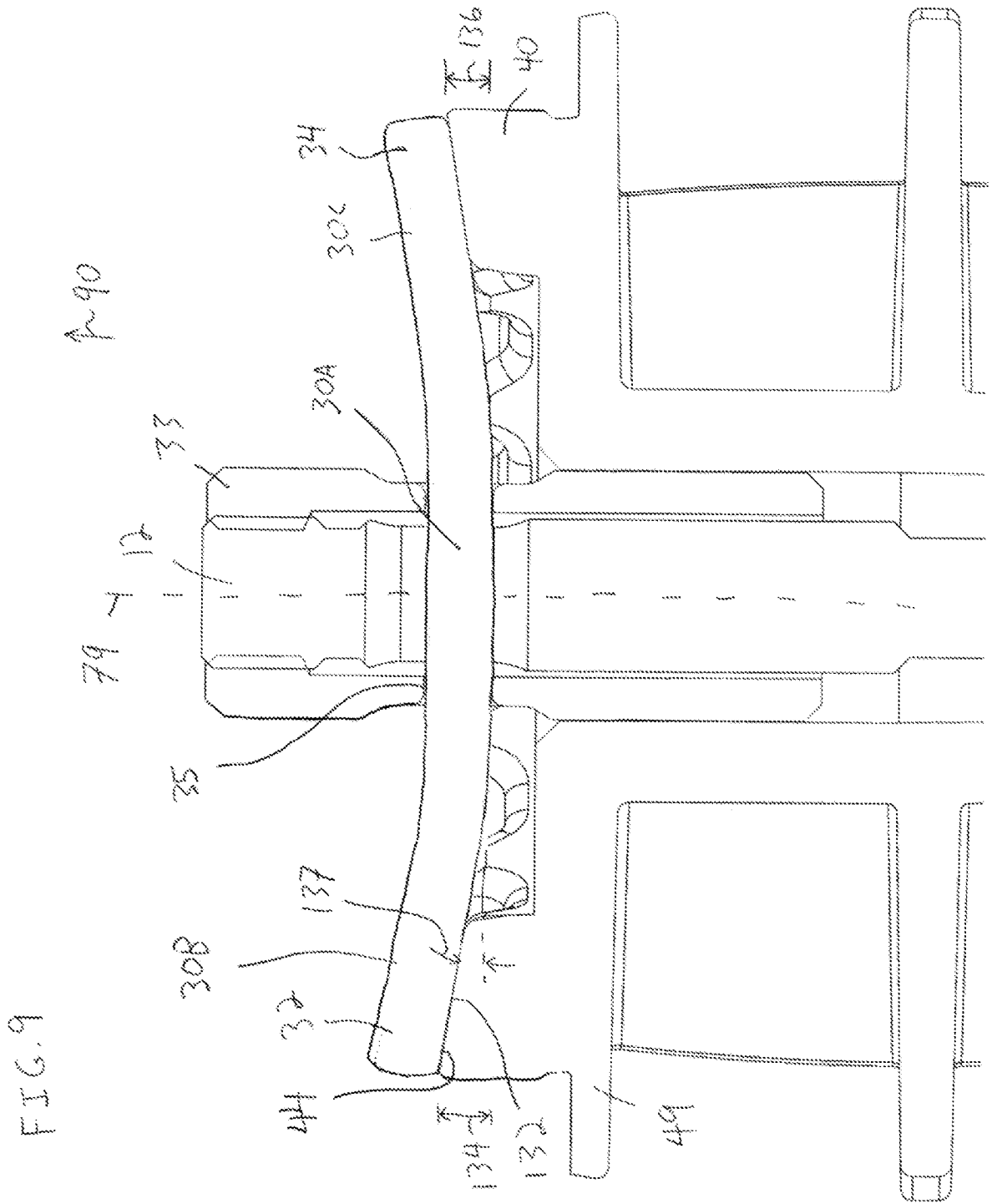
FIG. 9 is a view similar to FIG. 8 showing free ends of the pin deflected upward by the raised ridges of the handle body in response to torque being applied to the handle.
Figure 14:
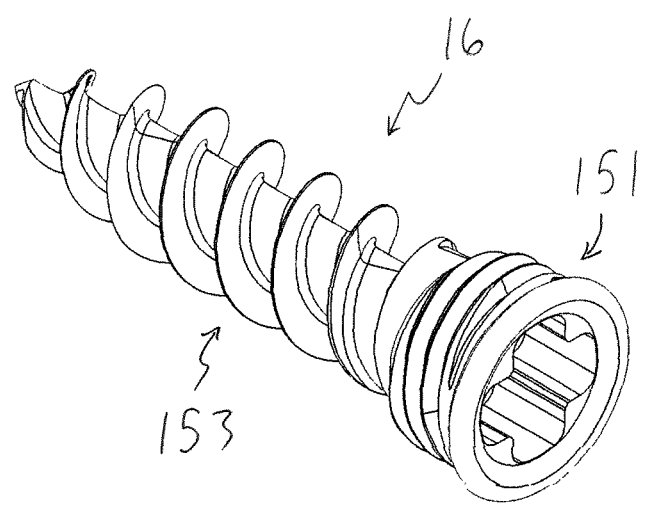
FIG. 14 is a perspective view of a bone screw that may be used with the driver of FIG. 1 or FIG. 12.

With reference to FIGS. 1 and 2, a torque-limiting driver 10 is provided that includes a shaft 12 with a distal end portion 14 adapted to be connected to, for example, a bone screw 16 (see FIG. 14), a set screw of a bone plate, a pedicle screw, or another torque to lock device. The driver 10 includes a handle 18 rotatably connected to a proximal end portion 20 of the shaft 12. The driver 10 allows a user to turn the handle 18 in direction 22 and cause the shaft 12 to also turn in direction 22 about longitudinal axis 79 to drive, for example, a bone screw into bone. With reference to FIGS. 2 and 3, the driver 10 has a torque limiting mechanism 27 that includes a resilient detent member, such as a resilient elongate pin 30, which is operable so that turning of the handle 18 likewise causes turning of the shaft 12. The torque limiting mechanism 27 disengages the handle 18 from the shaft 12 once the torque applied to the handle 18 exceeds a predetermined torque limit for the driver 10 so that handle 18 rotates relative to the shaft 12. This keeps the shaft 12 from applying torque to the bone screw that exceeds the torque limit of the driver 10. In one form, the pin 30 deflects to disengage the handle 18 from the shaft 12 once the torque applied to the handle 18 exceeds the predetermined torque limit for the driver 10. The pin 30 may be of a metallic material, such as nitinol, and may have super-elastic properties. With reference to FIGS. 8 and 9, an intermediate portion 30A of the pin 30 extends through the shaft 12 and a nut 33 threadingly engaged with the shaft 12. The pin intermediate portion 30A is held against upward or downward movement by the nut 33. The pin 30 has halves 30B, 30C extending outward from openings 35 of the nut 33 that are deflected by the handle 18 and each operate as a cantilever beam as torque is applied to the handle 18. In another form, the resilient detent member has only one portion extending outward from the shaft 12 and contacting the handle 18.

Figure 4:
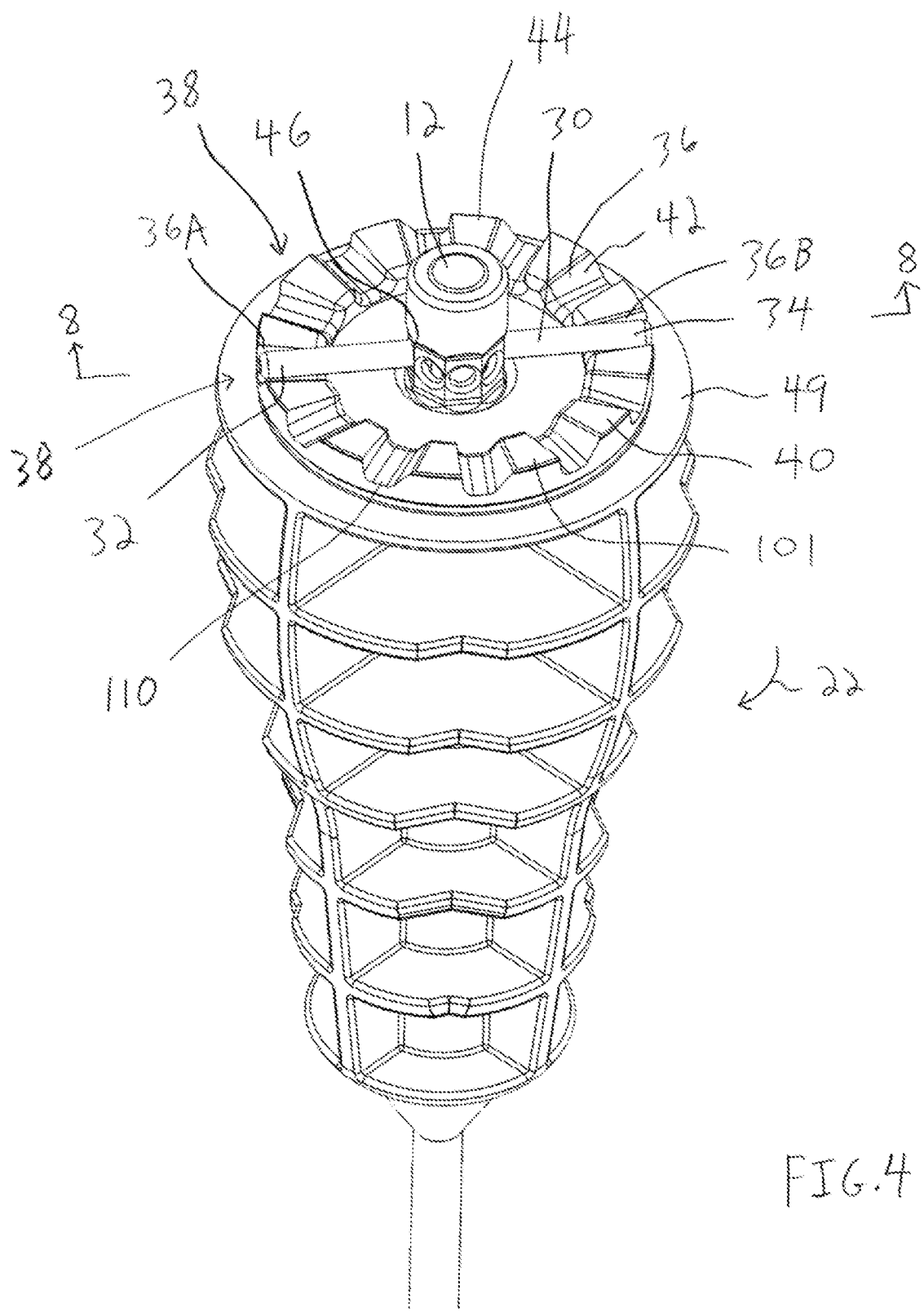
FIG. 4 is a perspective view of the driver of FIG. 1 with the cap of the handle removed to show the pin extending radially outward from the nut into a pocket structure of the handle.

Turning to FIG. 4, the pin 30 has ends portions 32, 34 sized to be received in pockets 36 of a contiguous pocket structure 38 of the handle 18. The pocket structure 38 includes raised ridges 40 and the pin end portions 32, 34 move over the raised ridges 40 when the torque applied to the handle 18 exceeds the predetermined torque limit for the driver 10. More specifically, as the handle 18 is turned in direction 22 to drive the bone screw or other element engaged with the shaft 12 into bone, the pin end portions 32, 34 engage ramp surfaces 42 of the ridges 40 and the pin 30 resists further turning of the handle 18 about the shaft 12. The pin 30 may deflect and bend in response to the torque applied to the handle 18. The ramp surfaces 42 deflect the end portions 32, 34 in both a rotary direction (see FIGS. 6 and 7) and an axial direction (see FIGS. 8 and 9), as discussed in greater detail below. Although the pin 30 deflects, the pin 30 transfers the torque applied to the handle 18 to the shaft 12 which, in turn, transfers the torque to the bone screw 16. The driver 10 may be used in non-surgical applications, such as in, for example, the automotive and bicycle fields of endeavor.

Once the torque the user is applying to the handle 18 reaches the predetermined torque limit for the driver 10, the pin end portions 32, 34 deflect up onto lands or upper surfaces 44 of the ridges 40. The ridge upper surfaces 44 slide beneath the pin end portions 32, 34 as the user continues to turn the handle 18 which allows the handle 18 to turn relative to the shaft 12. Once the handle 18 has turned far enough to align the pin end portions 32, 34 with the next pockets 36, the pin end portions 32, 34 are no longer held in an upwardly deflected position by the ridges 40 and rebound downward into the next pockets 36. The pin end portions 32, 34 rebound downward and strike lower surfaces, such as floor surfaces 110, of the next pockets 36. The impact of the pin end portions 32, 34 provide an audible and tactile indication to the user that the user has reached the predetermined torque limit for the driver 10. Further, because the pin end portions 32, 34 are in the next pockets 36, the user may move the driver 10 to another bone screw and again turn the handle 18 in direction 22 to drive the bone screw into bone until the predetermined torque limit has been reached. In this manner, the driver 10 may be used to quickly drive several bone screws or other elements one after the other using the same torque output.

With reference to FIGS. 2 and 3, the driver 10 includes a nut 33 having a threaded engagement 33A with the proximal portion 20 of the shaft 12. The nut 33 has one or more pairs of diametrically opposed through openings 35 that can be aligned with a through opening 46 of the shaft 12 by turning the nut 33 about the shaft 12. The pin 30 extends through one of the nut openings 35, through the shaft opening 46, and through an opposed nut opening 35. The nut openings 35 are sized to form a slip fit connection with the pin 30. By turning the nut 33 about the shaft 12 during assembly (and before inserting the pin 30), the axial position of the nut 33 can be set which in turn sets the axial position of the pin 30 once the pin 30 has been inserted through the nut openings 35 and the shaft opening 46. Further, adjusting the axial position of the pin 30 within the pockets 36 allows the manufacturer to set the predetermined torque limit for the driver 10. More specifically, positioning the pin free end portions 32, 34 axially lower in pockets 36 requires the pin free end portions 32, 34 to travel farther in the axial and rotary directions up the ramp surfaces 42 before reaching the upper surfaces 44. The material of the pin 30 must deflect a greater distance to permit this farther deflection of the pin end portions 32, 34. The increased deflection of the pin 30 translates into a higher predetermined torque limit for the driver 10. Conversely, positioning the pin free end portions 32, 34 axially higher in the pockets 36 requires the pin free end portions 32, 34 to travel a shorter distance in axial and rotary directions up the ramp surfaces 42 before reaching the upper surfaces 44. The material of the pin 30 has to deflect a smaller distance which translates into a lower predetermined torque limit for the driver 10.

The handle 18 includes a handle body 49 and a cap 50 that is connected to the handle body 49. The handle body 49 is captured between the pin 30 and a seat 51 of the shaft 12. In one form, the handle body 49 is made of Radel® plastic and the shaft 12 is made of a metal, such as stainless steel. The handle body 49 has a surface 49A that contacts a surface 51A of the shaft seat 51. The materials of the handle body 49 and shaft 12 as well as the geometry of the interface between surfaces 49A, 51A may be selected to minimize frictional resistance to turning of the handle body 49 relative to the shaft 12. Although users may press downwardly in direction 92 with varying amounts of pressure, the operation of the pin 30 and ridges 40 is unaffected by high pressure or low pressure applied to the handle body 49. In other words, the torque required to deflect the pin free ends 32, 34 over the ridges 40 is generally independent of the pressure the user is applying to handle 18 in direction 92. In one form, a low friction bushing such as a Teflon® bushing can be used to further limit friction between the handle 18 and the shaft 12.

The cap 50 keeps debris out of the torque limiting mechanism 27. In one form, the cap 50 has an annular wall 52 and an inner surface 60 thereof that resists movement of the pin 30 in directions 62. The cap 50 thereby keeps the pin 30 extending through the nut 33 and shaft 12 which, in turn, axially constrains the handle body 49 between the pin 30 and the shaft seat 51. In some forms, there is a gap between each pin end portion 32, 34 and the annular wall 52 during normal operation of the driver 10 so that there is no contact between the pin 30 and the cap 50 that can affect the torque limit of the driver 10.

The cap 50 may have a lip 54 extending inwardly from the wall 52 that engages a groove 56 (see FIG. 5) of the handle body 49. The engagement between the lip 54 and the groove 56 forms a snap-fit that retains the cap 50 on the handle body 49. In another form, the cap 50 and handle body 49 may be chemically welded together or secured together using fastener(s). The cap 50 and the handle body 49 may be made from the same or different materials, including plastics such as Radel® and polyether ether ketone (PEEK) and including metallic materials such as aluminum and stainless steel. One or more of the components of the driver 10 may be, for example, injection molded, machined, or 3D printed.

With reference to FIG. 3, the handle body 49 includes an inner sleeve 72 with a through opening 70 sized to receive the upper portion 20 of the shaft 12. The handle body 49 has vertical webs 74 and horizontal webs 74 extending outward from the inner sleeve 72. The webs 74, 76 form a grid-like outer shape of the handle body 49 with recesses 78. The fingers of a user may extend around outer portions of the webs 74, 76 and into the recesses 78 as the user grasps the handle 18.

Figure 5:
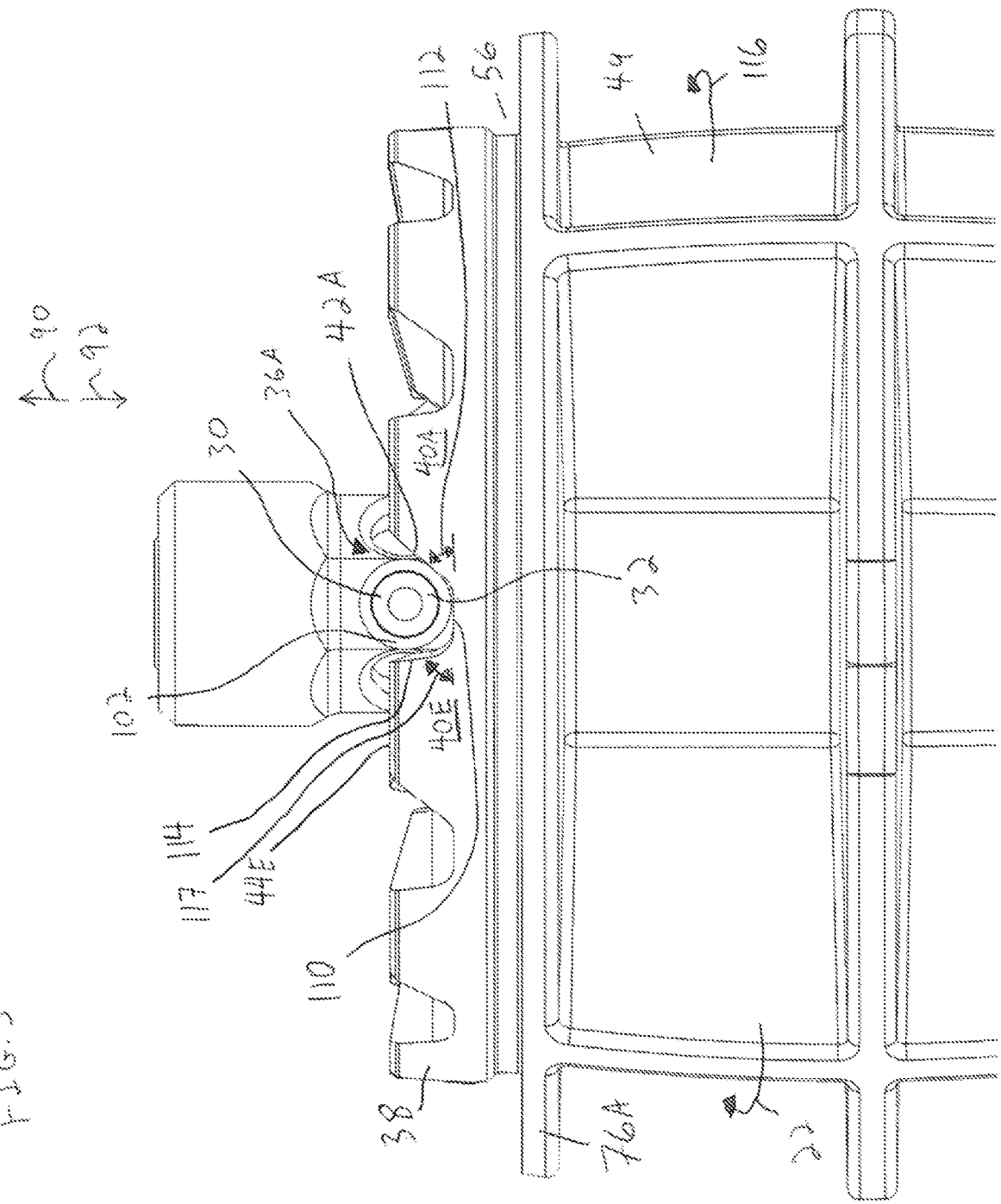
FIG. 5 is a side elevational view of the driver of FIG. 4 showing one end of the pin received in a pocket of the pocket structure.

With reference to FIGS. 4 and 5, the pin 30 may extend radially outward from the shaft 12 and position the pin end portions 32, 34 in the pockets 36A, 36B. The handle body 49 includes a torque limiting portion 100 having a the contiguous pocket structure 38 including the recessed pockets 36 and the raised ridges 40. The contiguous pocket structure 38 has an annular shape with the pockets 36 and ridges 40 arranged in a continuous, uninterrupted pattern of one pocket 36 followed by one ridge 40, followed by one pocket 36, etc. around the contiguous pocket structure 38. The contiguous pocket structure 38 allows a user to quickly and easily apply the maximum predetermined torque permitted by the driver 10 to one surgical device after another. For example, the surgical driver 10 may be used to sequentially drive a first bone screw into bone until the torque applied to the handle 18 reaches the predetermined torque limit, drive a second bone screw into bone until the torque applied to the handle 18 reaches the predetermined torque limit, and tighten a set screw on a bone plate to the predetermined torque limit. The user can perform these operations quickly in sequence without having to re-calibrate the driver 10 before each operation.

With reference to FIG. 5, the pocket 36A and the ridge 40A will be discussed in greater detail, although the remainder of the pockets 36 and ridges 40 may be identical to the pocket 36A and ridge 40A. The pocket 36A includes an upper opening 102 through which the pin 30 shifts downward into the pocket 36A in direction 92 and upwardly in direction 90 out of the pocket 36A. Prior to a user applying torque to the handle 18, the pin 30 has an initial, undeflected configuration wherein the pin 30 is straight and the pin end portion 32 is received in the pocket 36A. The pin end portion 32 is spaced from the surfaces of the pocket 36A including the floor surface 110 and the ramp surface 42A. The pin end portion 34 is likewise received in the pocket 36B (see FIG. 6) spaced from the surfaces of the pocket 36B such that the handle body 49 does not apply a load against either end portion 32, 34. Because the pin end portions 32, 34 are spaced from the surfaces of the pockets 36A, 36B, the handle body 49 generally does not apply a load against the pin 30 when the driver 10 is not in use. The lack of loading against the pin 30 limits the creep in the material of the pin 30 such as during transport or storage. Creep in the material in the form of permanent set of the pin 30 could change the properties of the pin 30 and change the predetermined torque limit of the driver 10.

The ridge 40A includes a ramp surface 42A oriented at an angle 112 relative to the floor 110. The angle 112 may be in the range of approximately 25 degrees to approximately 75 degrees, such as 50 degrees. The ramp surfaces 42 may each be a planar, inclined surface. In another form, the ramp surfaces 42 each have a curvature such as being concave or convex. The ramp surfaces 42 may also have a complex helical shape. The ramp surfaces 42 may have surface portion(s) configured to affect the frictional resistance to movement of the pin 30 along the ramp surfaces 42, such as projections, recesses, or other structures. The materials of the pin 30 and handle body 49 may be, for example, super elastic nitinol and Radel® plastic, and the coefficient of friction between the materials selected to contribute to the predetermined torque limit of the driver 10.

The ridge 40E is on an opposite side of the pocket 36A from the ramp surface 42A and includes a vertical surface 114. The vertical surface 114 contacts the pin 30 if the handle 18 is turned in a loosening direction 116. The vertical surface 114 extends at angle 117 relative to the floor surface 110 that is larger than the angle 112. In one form, the angle 117 is in the range of approximately 68 degrees to approximately 128 degrees, such as 98 degrees. The angle 117 is larger than angle 112 so that the vertical surface 114 extends more vertically than the ramp surface 42A. In this manner, the vertical surface 114 engages the pin 30 when the user turns the handle 18 in loosening direction 116 and permits the user to turn an element, such as a bone screw, in direction 116. Due to the more vertical profile of vertical surface 114, the vertical surface 114 generally does not cam the pin 30 upwardly in direction 90 such that the pin 30 remains operatively engaged with the handle body 49. This allows the user to apply a higher amount of torque to the handle 18 in direction 116 than in direction 22. In one form, the vertical surface 114 and angle 117 are configured to cam the pin end portion 32 up onto the ridge 40E in response to the torque applied to the handle in direction 116 exceeding a second predetermined torque limit. The first and second predetermined torque limits that may be applied by turning the handle 18 in directions 22, 116 may be the same or different, and may be tailored to a particular application.

Figure 6:
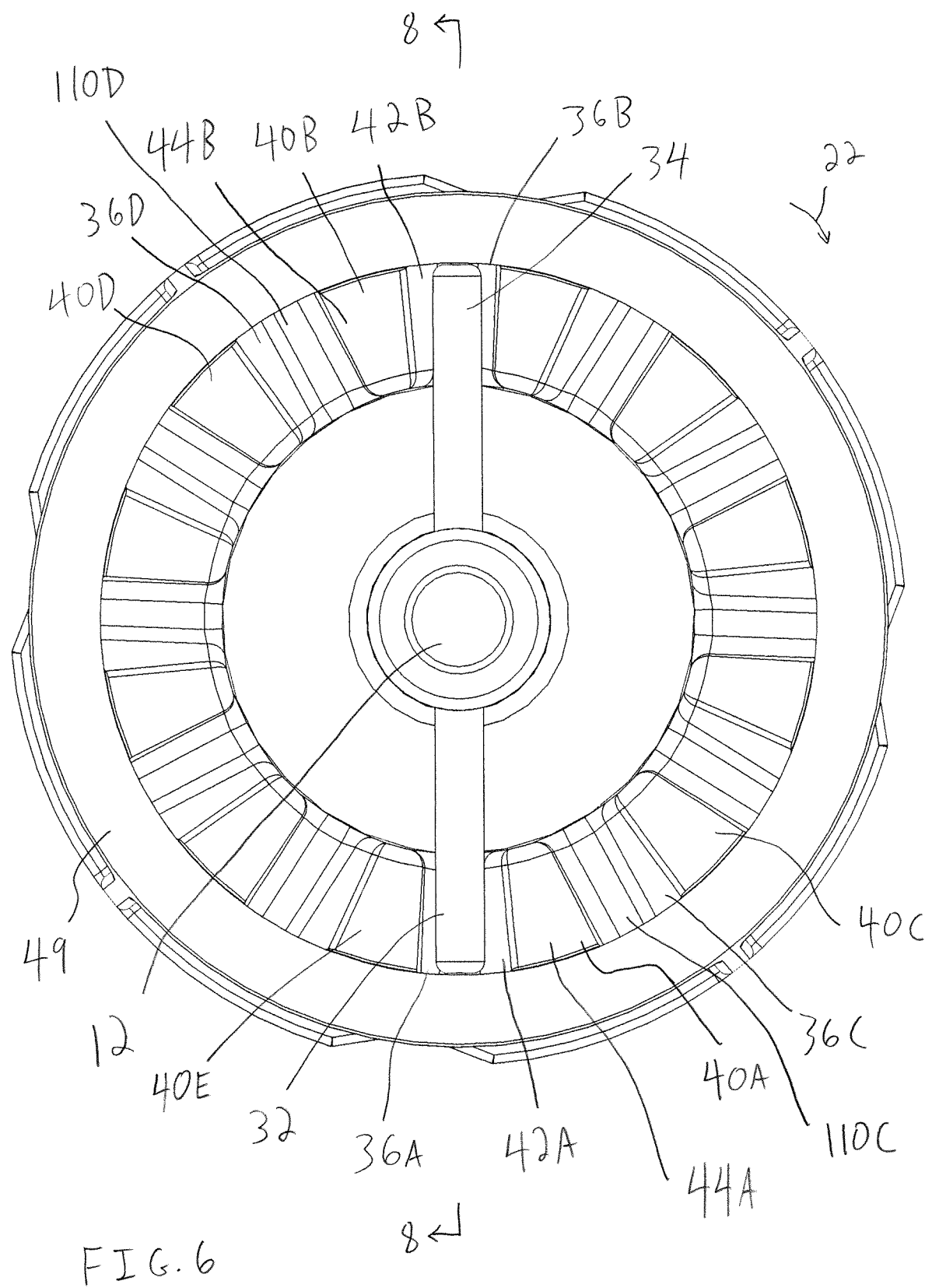
FIG. 6 is a top plan view of the driver of FIG. 4 showing the pin in an undeflected configuration before torque is applied to the handle.
Figure 7:
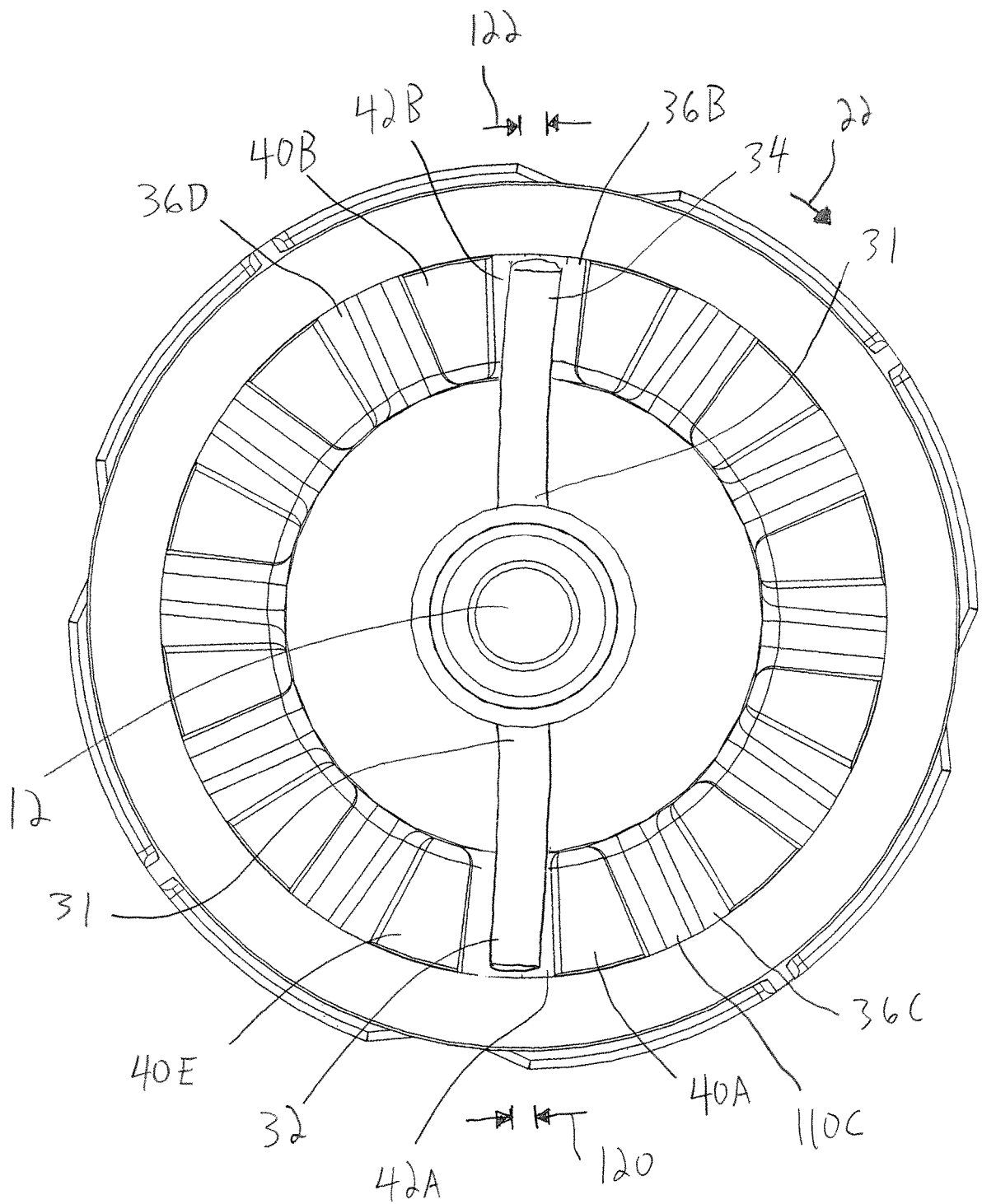
FIG. 7 is a view similar to FIG. 6 showing the handle body turned clockwise about the shaft in response to torque being applied to the handle and raised ridges of the handle body deflecting the pin.

With reference to FIGS. 6 and 7, turning the handle 18 in tightening direction 22 to drive an element imparts rotary deflection to the pin 30 by shifting the end portions 32, 34 in direction 22. More specifically, the pin 30 is straight and extends radially outward from the shaft 12 prior to a user applying a torque to the handle 18 as shown in FIG. 6. Once the user has connected the shaft 12 with an element, such as a bone screw engaged with bone, turning the handle 18 in direction 22 causes the ramp surfaces 42A, 42B to rotationally shift the pin end portions 32, 34 as shown in FIG. 7. This deflects the end portions 32, 34 distances 120, 122 from the initial positions thereof in the rotary direction 22.

Turning to FIGS. 8 and 9, the ridges 40 will be discussed in greater detail. In the initial, undeflected configuration, the pin 30 has a central longitudinal axis 121 extending perpendicular to the longitudinal axis 79 of the shaft 12 as shown in FIG. 8. As the user applies torque to the handle 18, the ramp surfaces of the ridges 40 bend the pin end portions 32, 34 axially upward in direction 90 as the pin end portions 32, 34 reach the ridge upper surfaces 44. In FIG. 9, the pin end portions 32, 34 are shown having reached the ridge upper surfaces 44 after the torque limit of the driver 10 has been reached. The ridge upper surfaces 44 extend at an angle 137 from an axis perpendicular to the shaft longitudinal axis 79. Thus, in order for the pin end portions 32, 34 to reach the ridge upper surfaces 44, the pin end portions 32, 34 are deflected distances 134, 136 in the axial direction. This required axial deflection of the pin 30 contributes to setting the torque limit for the driver 10. For example, larger axial distances 134, 136 require more torque to be applied to the handle 18 and smaller axial distances 134, 136 require less torque to be applied to the handle 18.

The predetermined torque limit provided by the driver 10 is a resultant of the force required to strain the pin 30 in two directions, i.e., in the axial and rotary directions, plus the frictional resistance between the pin end portions 32, 34 and the ramp surfaces 42 of the handle body 49. These parameters may be adjusted to provide a particular predetermined torque limit for the driver 10.

With reference to FIGS. 6-9, a method of using the surgical driver 10 to drive an element, such as a bone screw, is provided to show the axial and rotational deformation that occurs in the pin 30 as the pin 30 limits the torque applied to the bone screw.

In FIG. 6, the cap 50 of the driver tool 10 is removed to show the shaft 12, the handle body 49, and the pin 30 in the initial configuration prior to a user turning the handle 18 in the tightening direction 22. The pin end portions 32, 34 are received in the pockets 36A, 36B and are spaced from the associated ramp surfaces 42A, 42B. With reference to FIG. 8, the shaft 12, handle body 49, and pin 30 are in the initial configuration before the user applies turns the handle 18 in direction 22. With the driver 10 in the initial configuration, the user may connect the distal end portion 14 of the shaft 12 to a head portion 151 (see FIG. 14) of the bone screw 16 and position a shank portion 153 of the bone screw against a bone.

The user then turns the handle 18 in direction 22, which turns the handle body 49 about the shaft 12 as shown in FIG. 7. The movement of the handle body 49 around the shaft 12 brings the ramp surfaces 42A, 42B into engagement with the pin end portions 32, 34. The ramp surfaces 42A, 42B shift the pin end portions 32, 34 in rotary direction 22 with the handle body 49. The pin 30 resists the pin end portions 32, 34 deflecting in the rotary direction 22 which provides resistance to turning of the handle body 49 relative to the shaft 12. The pin end portions 32, 34 deflect the rotary distances 120, 122 before the ramp surfaces 42, 42B cam the end portions 32, 34 upward onto the upper surfaces 44A, 44B of the ridges 40A, 40B. In this manner, each half of the pin 30 achieves a first maximum type of strain due to movement of the pin end portions 32, 34 in the rotary direction 22 before the pin end portions 32, 34 may shift upward onto the wall upper surfaces 44A, 44B.

The halves of the pin 30 also achieve a second maximum strain due to the ridge ramp surfaces 42A, 42B camming the pin end portions 32, 34 axially upward in direction 90. With reference to FIG. 9, the ramp surfaces 42 cam the pin end portions 32, 34 axially upward distances 134, 136 in direction 90 from the initial positions thereof (see FIG. 8) to fully deflected positions thereof (see FIG. 9). The pin end portions 32, 34 must be deflected to the fully deflected positions before the ridge upper surfaces 44 may slide beneath the pin end portions. In this manner, each half of the pin 30 achieves the second maximum type of strain due to the movement of the pin end portions 32, 34 in the axial direction 90 before the pin end portions 32, 34 shift onto the ridge upper surfaces 44A, 44B.

In the fully deflected position of the pin end portions 32, 34, the ridges 40 orient the pin end portions 32, 34 to extend at the angle 137 (see FIG. 9) from the undeflected, horizontal orientation (see FIG. 8). The torque limit for the driver 10 may be tailored by configuring the ridges 40 to bend the pin portions 32, 34 so that the pin portions 32, 34 extend at larger or smaller angles 137. For example, by increasing the angle 137 of the fully deflected position of the pin end portions 32, 34, the pin 30 is subjected to more strain in the pin 30 to climb the ramp surfaces 42 and increases the torque limit of the driver 10. Conversely, decreasing the angle 137 of the fully deflected position of the pin end portions 32, 34 reduces the strain in the pin 30 and reduces the torque limit of the driver 10.

Once the user applies torque to the handle 18 that exceeds the torque limit of the driver 10, the pin end portions 32, 34 shift off of the ramp surfaces 42A, 42B and onto the upper surfaces 44A, 44B of the ridges 40A, 40B. When the pin end portions 32, 34 shift off of the ramp surfaces 42A, 42B, the pin end portions 32, 34 offer much less resistance to movement of the ridges 40A, 40B past the end portions 32, 34 in the rotary direction 22. Despite this sudden decrease in resistance, the user continues to apply torque to the handle 18 which causes the handle 18 to turn farther around the shaft 12 in direction 22 and slides the ridge upper surfaces 44A, 44B below the pin end portions 32, 34.

Figure 10:
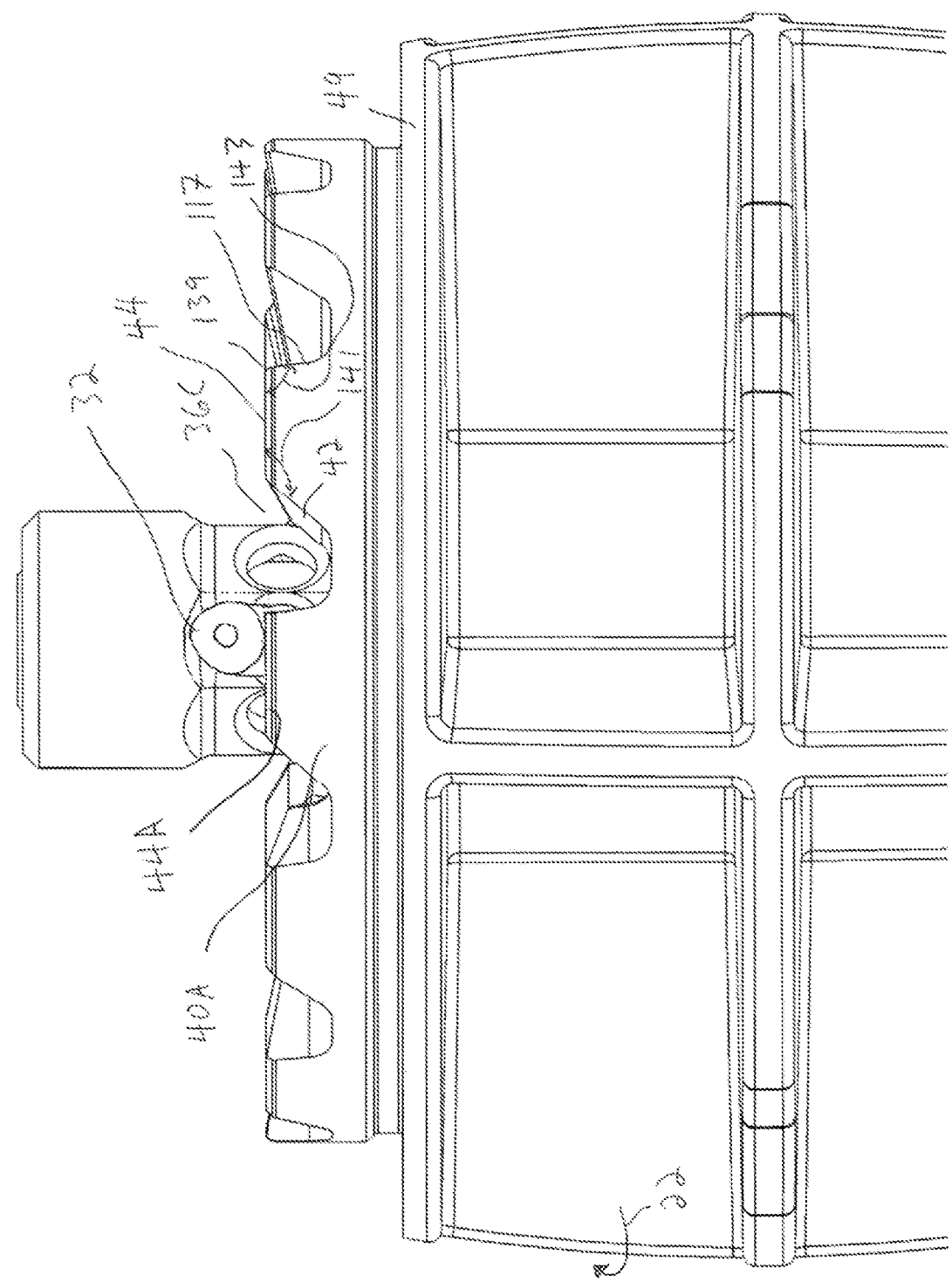
FIG. 10 is a side elevational view similar to FIG. 5 showing one of the free ends of the pin on top of one of the raised ridges of the handle body after a predetermined maximum torque has been applied to the handle.

With reference to FIG. 10, the ridge upper surface 44A is shown sliding beneath the pin end portion 32 as the user continues to turn the handle 18 in direction 22 after the pin end portions 32, 34 have shifted onto the upper surfaces 44A, 44B of the ridges 40A, 40B. The ridges 40 each include a corner 139 between the upper surface 44 and the vertical surface 117. In one form, the corner 139 is a substantially right angle corner having an angle 143 that is in the range of approximately 68 degrees to approximately 128 degrees, such as 98 degrees. The angle 143 is smaller than the angle 141 between the ramp surface 42 and the upper surface 44, with the angle 141 being in the range of approximately 100 degrees to approximately 160 degrees, such as 130 degrees. The angle 143 is smaller than the angle 141 to provide an abrupt drop-off for the pin 30, which allows the pin ends 32, 34 to quickly increase velocity as they shift off the ridges 40 and maximize the force of impact against the floor surfaces 110.

Figure 11:
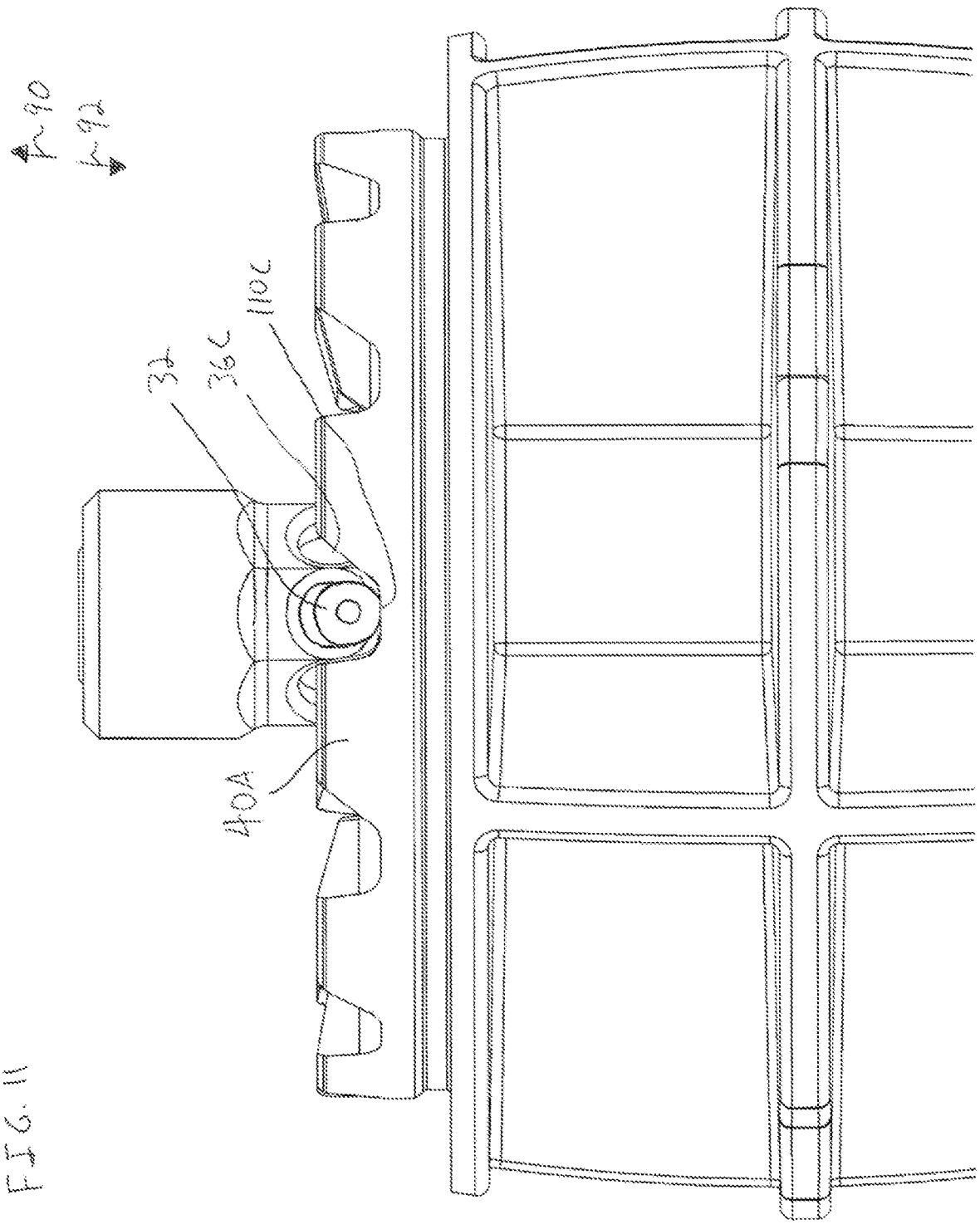
FIG. 11 is a side elevational view similar to FIG. 10 showing the pin free end snapping downward from the raised ridge against a lower surface of the handle body.

The user continues to turn the handle 18 in direction 22 until the pin end portions 32, 34 reach the next pockets 36C, 36D. Once the ridges 40A, 40B turn past the pin end portions 32, 34, the pin end portions 32, 34 can rebound from the deflected configurations thereof and the pin 30 can return to the undeflected, straight configuration thereof. With reference to FIG. 11, the pin end portions 32, 34 snap downward in direction 92 into the pockets 36C, 36D as the pin 30 rebounds. The pin end portions 32, 34 travel in vertical direction 92 beyond their initial vertical positions and strike the floor surfaces 110C, 110D of the pockets 36C, 36D. The impact of the end portions 32, 34 against the floor surfaces 110C, 110D provides audible and tactile feedback to the user that the driver 10 has reached the torque limit for the driver 10. The end portions 32, 34 bounce back upward in direction 90 away from the floor surfaces 110C, 110D to their initial, undeflected vertical positions wherein the end portions 32, 34 are spaced from the surfaces of the pockets 36C, 36D. The user may then move the driver 10 to the next bone screw, lock nut, etc. and the process is repeated to torque the next bone screw, lock nut, etc. to the torque limit of the driver 10.

The predetermined torque limit for the driver may be in the range of, for example, approximately 5 inch-pounds to approximately 35 inch-pounds, such as 20 inch-pounds. As discussed above, the driver 10 may be used repeatedly to torque different elements to the maximum torque permitted by the driver 10. As one example, the driver 10 may be used to secure four bone plates to a sternum with each bone plate having four bone screws and at least one set screw. The driver 10 would in this example be used to drive at least 16 bone screws and four set screws. The driver 10 could be discarded after use.

The driver 18 may be configured to permit a user to apply different maximum torque to different devices. For example, the first three ridges 40 the pin end portions 32, 34 encounter may be identical and be configured to require ten inch-pounds for the pin end portions 32, 34 to deflect over the ridges 40. The next ridge 40 that each pin end portions 32, 34 encounter may be different than the first three end portions 40, with the next ridge 40 requiring fifteen inch-pounds for the pin end portions 32, 34 to deflect over the ridge 40. Further, the ridges 40 can be shaped to present different torque profiles, such as offering less resistance initially to the pin end portions 32, 34 and then sharply increasing resistance. Each ridge 40 or pocket 36 can have a different geometry to provide a different maximum torque and torque profile as desired for a particular application.

Figure 12:
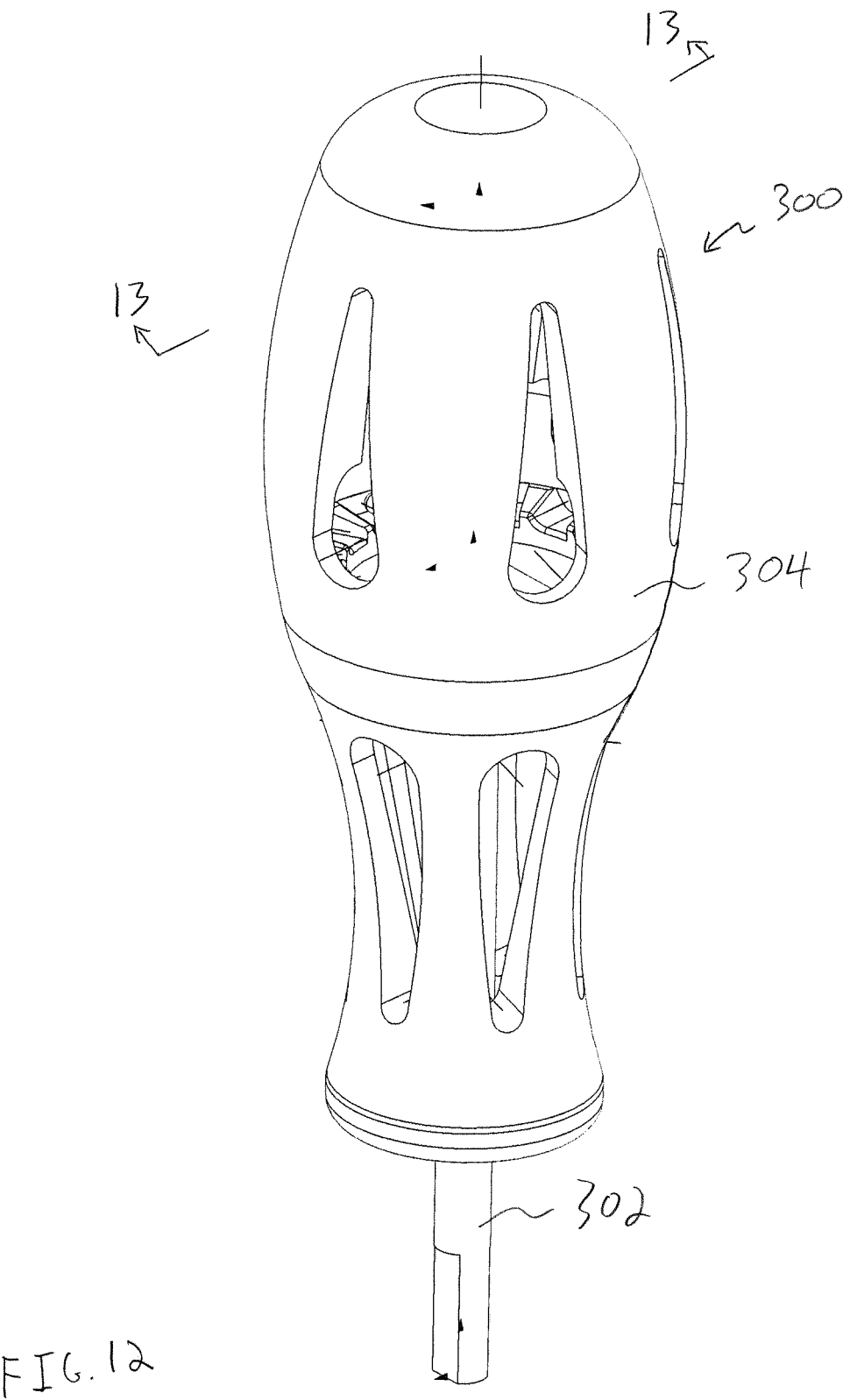
FIG. 12 is a perspective view of a torque limiting surgical driver having a handle and a shaft.
Figure 13:
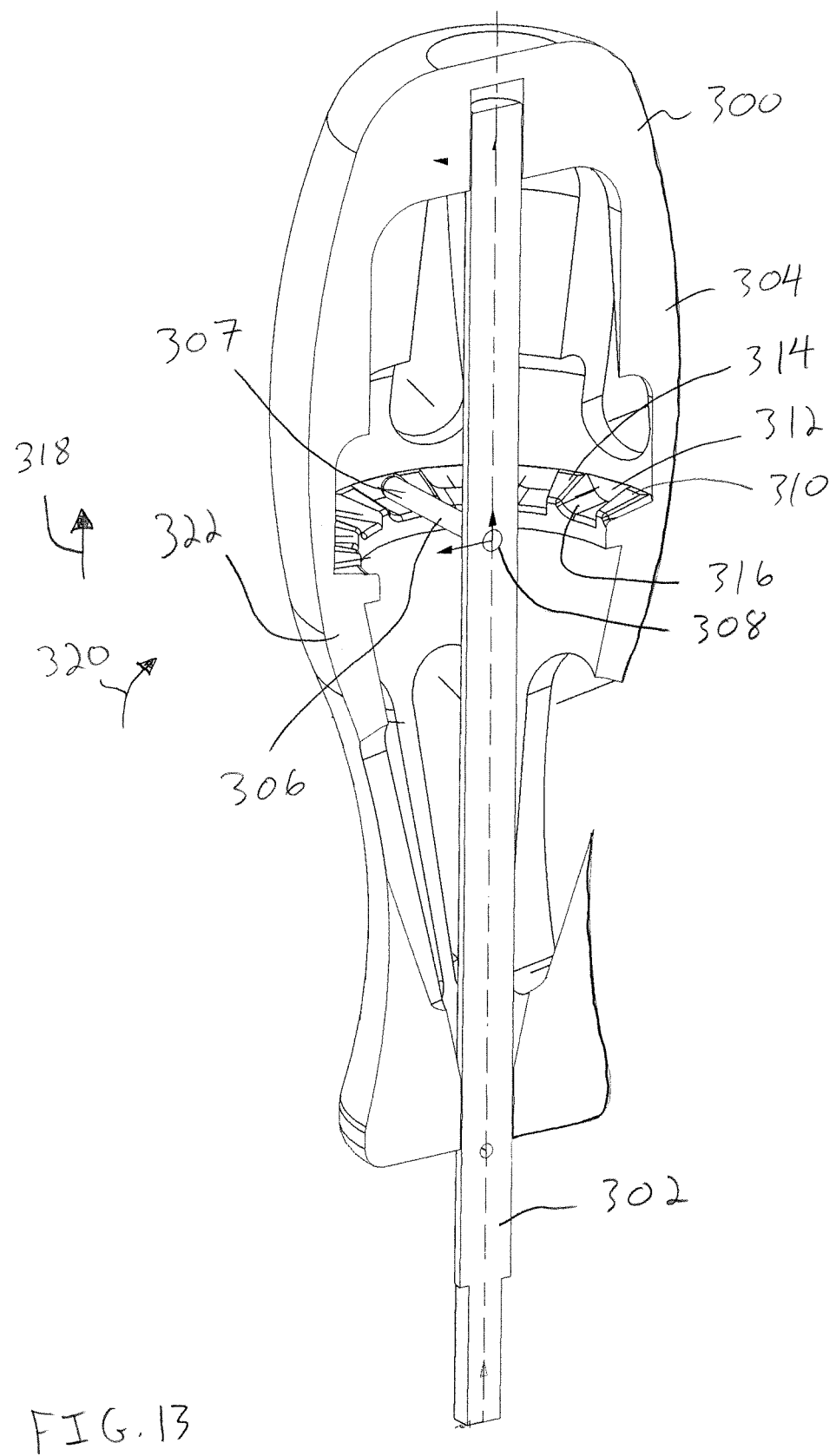
FIG. 13 is a cross-sectional view taken across line 13-13 in FIG. 12 showing the handle of the driver extending around the shaft of the driver.

With reference to FIG. 12, another torque limiting driver 300 is provided that is similar in many respects to the driver 10 discussed above. The driver 300 includes a shaft 302 and a handle 304 that is rotatable relative to the shaft 302. With reference to FIG. 13, the driver 300 includes a pin 306 extending through a through opening 308 of the shaft 302. The handle 304 includes an internal contiguous structure 310 including pockets 312 and ridges 314. The pin 306 includes opposite end portions 307 each received in a diametrically opposed pocket 312. The ridges 314 have ramp surfaces 316 that deflect the pin end portions 307 in an axial direction 318 and a rotary direction 320 as the handle 304 is turned in direction 320. In this manner, the pin end portions 307 shift out of respective pockets 312 in response to the torque applied to the handle 304 exceeding a predetermined value, which limits the torque the surgical driver 300 can apply to a member such as a bone screw or bone plate set screw. One difference between the driver 300 and the driver 10 is that the driver 300 does not include a cap for securing the pin 306 in the driver 300. Instead, the driver handle 304 includes a sidewall 322 that retains the pin 306 within the through opening 308 of the shaft 302.

Figure 15:
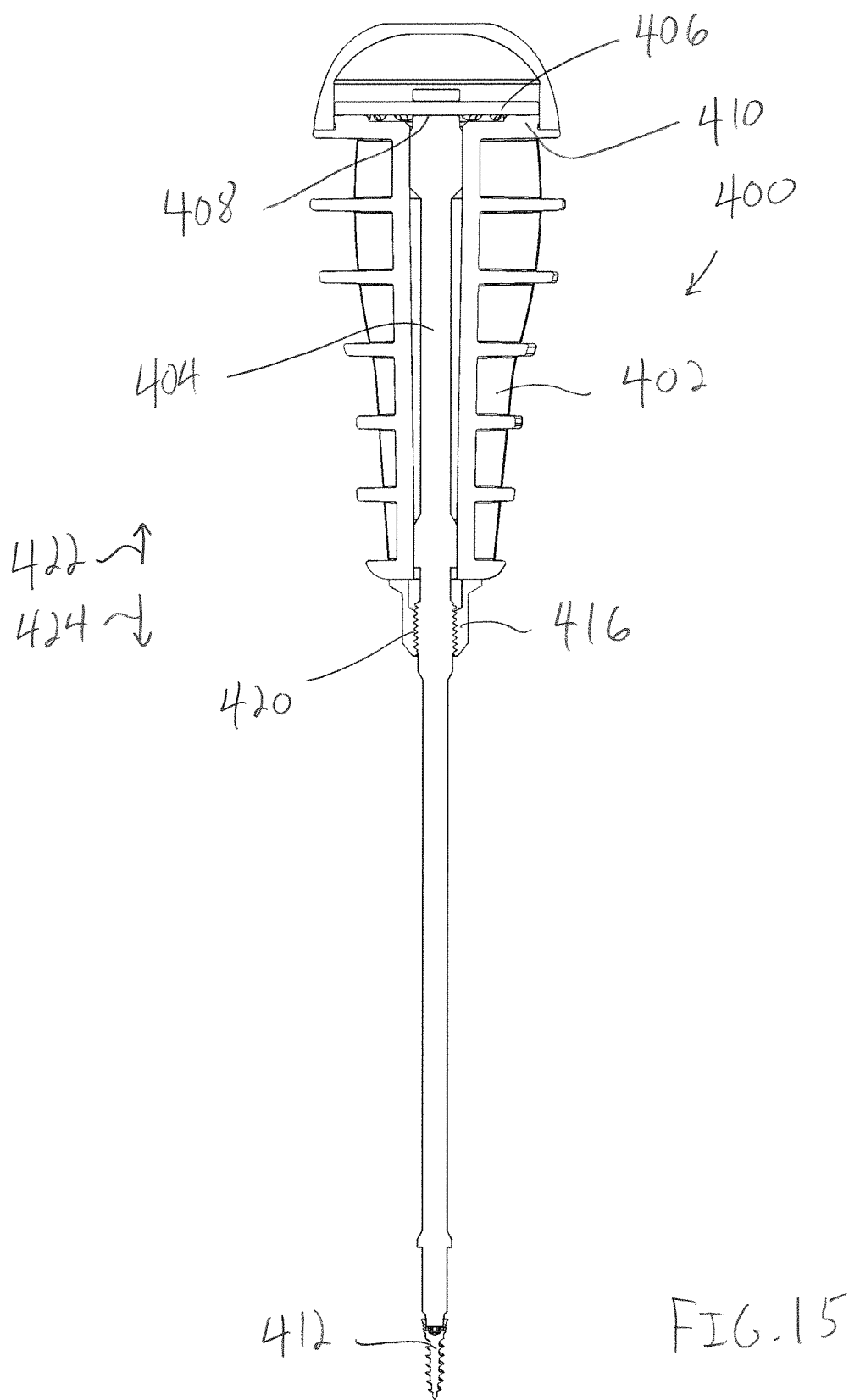
FIG. 15 is a cross-sectional view of a torque limiting surgical driver.

With reference to FIG. 15, another torque limiting driver 400 is provided that is similar in many respects to the driver 10 discussed above. The driver 400 includes a handle 402 rotatably connected to a shaft 404. The driver 400 has a resilient pin 406 extending through an opening 408 of the shaft 404. The resilient pin 406 has end portions that engage ridges 410 of the handle 410 and deflect to limit torque the driver 400 may apply to an element such as a bone screw 412.

One difference between the torque limiting drivers 10, 400 is that the driver 400 has a handle body 414 captured between the pin 406 and a nut 416. The nut 416 is connected to the shaft 404 at a threaded connection 420. The predetermined torque limit of the driver 400 may be adjusted by turning the nut 416, which shifts the handle body 414 in direction 422 or 424. Shifting the handle body 414 in direction 422 increases the torque limit of the driver 400 because the end portions of the pin 406 will sit lower in pockets associated with the ridges 410 such that the pin end portions will have to travel axially and rotationally farther to deflect over the ridges 410. Conversely, shifting the handle body 414 in direction 424 decreases the torque limit of the driver 400 because the pin end portions will sit higher in the pockets and will have to travel axially and rotationally shorter distances to deflect over the ridges 410. Because the nut 416 is threadingly engaged with the shaft 404, the torque limit of the driver 400 can be infinitely adjusted since the nut 416 is not limited to fixed positions along the shaft 404.

Those skilled in the art will recognize that a wide variety of modifications, alterations, and combinations can be made with respect to the above-described embodiments without departing from the spirit and scope of the invention, and that such modifications, alterations, and combinations are to be viewed as being within the scope of the claims.

What is claimed is:

1. A surgical driver comprising:
a driver shaft;
a handle rotatably connected to the driver shaft;
a resilient, elongate pin extending transverse to the driver shaft and operably engaged with the driver shaft and the handle such that torque applied to the handle for turning of the handle causes turning of the driver shaft, the pin being configured to deflect to limit the torque applied to the driver shaft.

2. The surgical driver of claim 1 wherein the pin has an initial configuration wherein the pin has a linear shape and a deflected configuration wherein the pin has a non-linear shape and applying torque to the handle deforms the pin from the initial configuration to the deflected configuration.

3. The surgical driver of claim 1 wherein the driver shaft includes a through opening and the pin extends through the through opening.

4. The surgical driver of claim 1 wherein the driver shaft includes a longitudinal axis and the pin includes a free end portion that deflects axially to permit the pin to limit the torque applied to the driver shaft.

5. The surgical driver of claim 1 wherein the pin extends perpendicular to the driver shaft and spans between the driver shaft and the handle.

6. The surgical driver of claim 1 wherein the pin is mounted to one of the driver shaft and the handle and the other of the driver shaft and handle includes pockets for receiving a portion of the pin, the pockets including ramp surfaces adapted to deflect and shift the pin portion out of the pocket to limit the torque applied to the driver shaft.

7. The surgical driver of claim 6 wherein the handle includes a body including the pockets and a cap connected to the body and extending about the pockets and the pin.

8. The surgical driver of claim 1 wherein the pin is of a superelastic metallic material.

9. The surgical driver of claim 1 wherein the handle has an annular wall and the elongate pin extends from the driver shaft to the annular wall.

10. The surgical driver of claim 1 wherein the shaft includes a shaft member and a sleeve extending about the shaft member, the sleeve and shaft member having through openings and the pin extends through the openings of the sleeve and shaft member.

11. A surgical driver comprising:
a driver shaft;
a handle rotatably connected to the driver shaft, the handle having a unitary, one-piece construction;
a resilient member operably engaged with the driver shaft and handle such that torque applied to the handle causes turning of the driver shaft, the resilient member being configured to deflect to limit torque applied to the driver shaft;
a plurality of spaced, raised ridge members of the handle adapted to deflect the resilient member upwardly to a deflected configuration as torque is applied to the handle, the raised ridge members each having a ramp surface for deflecting the resilient member upwardly and an upper surface along which the deflected resilient member travels as the handle turns relative to the driver shaft;
a vertical surface of each of the raised ridge members extending at a different inclination relative to the upper surface than the ramp surface;
a corner of each raised ridge member connecting the top surface and the vertical surface thereof; and
a lower surface extending between adjacent ones of the raised ridge members against which the resilient member strikes as the resilient member rebounds from the deflected configuration thereof.

12. The surgical driver of claim 11 wherein the corner connecting the top surface and the vertical surface of each raised ridge member is a substantial right angle corner.

13. The surgical driver of claim 11 wherein the upper surface of each raised ridge member is flat.

14. The surgical driver of claim 11 wherein the driver shaft has a longitudinal axis and the flat upper surfaces of the raised ridge members extend obliquely to the longitudinal axis.

15. The surgical driver of claim 11 wherein the raised ridge members are arranged in an annular pattern and the handle includes an annular wall extending around a radially outer circumference of the raised ridge members.

16. A surgical driver comprising:
a driver shaft;
a handle rotatably connected to the driver shaft;
a resilient member operably engaged with the driver shaft and handle such that torque applied to the handle causes turning of the driver shaft, the resilient member being configured to deflect to limit torque applied to the driver shaft;
a plurality of spaced, raised ridge members adapted to deflect the resilient member upwardly to a deflected configuration as torque is applied to the handle, the raised ridge members each having a ramp surface for deflecting the resilient member upwardly and an upper surface along which the deflected resilient member travels as the handle turns relative to the driver shaft;
a vertical surface of each of the raised ridge members extending at a different inclination relative to the upper surface than the ramp surface;
a corner of each raised ridge member connecting the top surface and the vertical surface thereof; and
a lower surface extending between adjacent ones of the raised ridge members against which the resilient member strikes as the resilient member rebounds from the deflected configuration thereof;
wherein the resilient member extends through an opening of the driver shaft.

17. The surgical driver of claim 16 wherein the corner connecting the top surface and the vertical surface of each raised ridge member is a substantial right angle corner.

18. The surgical driver of claim 16 wherein the upper surface of each raised ridge member is flat.

19. The surgical driver of claim 16 wherein the driver shaft has a longitudinal axis and the flat upper surfaces of the raised ridge members extend obliquely to the longitudinal axis.

20. The surgical driver of claim 16 wherein the raised ridge members are arranged in an annular pattern and the handle includes an annular wall extending around a radially outer circumference of the raised ridge members.

21. A surgical driver comprising:
a driver shaft;
a handle rotatably connected to the driver shaft;
a resilient member operably engaged with the driver shaft and handle such that torque applied to the handle causes turning of the driver shaft, the resilient member being configured to deflect to limit torque applied to the driver shaft;
a plurality of spaced, raised ridge members adapted to deflect the resilient member upwardly to a deflected configuration as torque is applied to the handle, the raised ridge members each having a ramp surface for deflecting the resilient member upwardly and an upper surface along which the deflected resilient member travels as the handle turns relative to the driver shaft;
a vertical surface of each of the raised ridge members extending at a different inclination relative to the upper surface than the ramp surface;
a corner of each raised ridge member connecting the top surface and the vertical surface thereof;
a lower surface extending between adjacent ones of the raised ridge members against which the resilient member strikes as the resilient member rebounds from the deflected configuration thereof; and
wherein the resilient member includes a pair of free end portions that engage different ones of the raised ridge members.

22. The surgical driver of claim 21 wherein the corner connecting the top surface and the vertical surface of each raised ridge member is a substantial right angle corner.

23. The surgical driver of claim 21 wherein the upper surface of each raised ridge member is flat.

24. The surgical driver of claim 21 wherein the driver shaft has a longitudinal axis and the flat upper surfaces of the raised ridge members extend obliquely to the longitudinal axis.

25. The surgical driver of claim 21 wherein the raised ridge members are arranged in an annular pattern and the handle includes an annular wall extending around a radially outer circumference of the raised ridge members.

26. A surgical driver having a longitudinal axis, the surgical driver comprising:
a driver shaft extending along the longitudinal axis;
a handle rotatably coupled to the driver shaft;
a resilient member operably engaged with the driver shaft and handle such that torque applied to the handle for turning the handle causes turning of the driver shaft;
a plurality of pockets each configured to receive the resilient member therein, each pocket including a ramp surface and a floor at a bottom of the ramp surface;
wherein the floors extend transverse to the longitudinal axis to limit axial movement of the resilient member;
the resilient member spaced from the floors of the pockets prior to the application of torque to the handle; and the ramp surfaces of the pocket surfaces adapted to deflect the resilient member out of the pockets to limit torque applied to the handle when the handle is turned.

27. The surgical driver of claim 26 wherein the ramp surfaces of the pockets are adapted to shift the resilient member axially out of the pocket as the torque applied to the handle exceeds the predetermined torque.

28. The surgical driver of claim 26 further comprising lands intermediate the pockets so that the deflected resilient member shifts out of the pockets and onto the lands.

29. The surgical driver of claim 26 wherein the handle includes the pockets and ramp surfaces thereof, the pockets having an annular arrangement extending about the driver shaft.

30. The surgical driver of claim 26 wherein the resilient member has a pair of free end portions received in two of the pockets without the resilient member contacting surfaces of the pockets prior to application of the torque to the handle.

31. The surgical driver of claim 26 wherein the resilient member has an initial, linear configuration and the resilient member has a deflected, non-linear configuration in response to torque being applied to the handle.

32. The surgical driver of claim 26 wherein the driver shaft has a longitudinal axis, the handle is fixed at an axial position relative to the driver shaft, and the resilient member includes a base portion mounted to the driver shaft at a fixed axial position.

\* \* \* \* \*